US006295986B1

(12) United States Patent
Patel et al.

(10) Patent No.: US 6,295,986 B1
(45) Date of Patent: Oct. 2, 2001

(54) REACTIVE ION ETCHING METHOD OF FABRICATING NOZZLES FOR AEROSOLIZED DELIVERY OF THERAPEUTIC OR DIAGNOSTIC AGENTS

(75) Inventors: Rajesh S. Patel; Sudarsan Srinivasan, both of Fremont, CA (US)

(73) Assignee: Aradigm Corporation, Hayward, CA (US)

(*) Notice: Subject to any disclaimer, the term of this patent is extended or adjusted under 35 U.S.C. 154(b) by 0 days.

(21) Appl. No.: 09/482,393

(22) Filed: Jan. 12, 2000

(51) Int. Cl.[7] .................................................. A61M 16/00
(52) U.S. Cl. ............................. 128/203.12; 128/203.23; 128/200.14; 128/203.22
(58) Field of Search ..................... 128/203.12, 203.23, 128/200.14, 203.22

(56) References Cited

U.S. PATENT DOCUMENTS

| | | | |
|---|---|---|---|
| 4,238,571 | * 12/1980 | Mano et al. ............................. 521/62 |
| 4,459,210 | * 7/1984 | Murakami et al. ................ 210/500.2 |
| 4,581,140 | * 4/1986 | Manabe et al. ..................... 210/500.2 |
| 4,919,810 | * 4/1990 | Itoh et al. ......................... 210/500.34 |
| 4,976,897 | * 12/1990 | Callahan et al. ........................ 264/22 |
| 5,022,990 | * 6/1991 | Doi et al. .......................... 210/500.42 |
| 5,079,272 | * 1/1992 | Allegrezza, Jr. et al. ............ 521/134 |
| 5,186,835 | * 2/1993 | Masuoka et al. ................ 210/500.36 |
| 5,286,324 | * 2/1994 | Kawai et al. ......................... 156/155 |
| 5,544,646 | 8/1996 | Lloyd et al. . |
| 5,590,383 | * 12/1996 | Sekhar et al. ............................. 419/2 |
| 5,660,166 | 8/1997 | Lloyd et al. . |
| 5,709,202 | 1/1998 | Lloyd et al. . |
| 5,718,222 | 2/1998 | Lloyd et al. . |
| 5,823,178 | 10/1998 | Lloyd et al. . |
| 5,829,435 | * 11/1998 | Rubsamen ....................... 128/203.21 |
| 5,906,202 | * 5/1999 | Schuster et al. ................ 128/203.23 |
| 5,934,272 | * 8/1999 | Lloyd et al. .................... 128/200.22 |
| 6,070,575 | * 6/2000 | Gonda et al. .................... 128/203.12 |

\* cited by examiner

*Primary Examiner*—John G. Weiss
*Assistant Examiner*—Mital Patel
(74) *Attorney, Agent, or Firm*—Karl Bozicevic; Paula A. Borden

(57) ABSTRACT

A method for producing a nozzle useful in generating a fine aerosol for delivery of a therapeutic or diagnostic agent is provided. The method comprises treating a thin, preferably flexible material having partially formed nozzles with a plasma which alters the size and shape of the nozzles. The pores in the nozzles so formed preferably have an unflexed exit aperture diameter in the range of about 0.5 to about 25 microns, depending on the size of the aerosol particles desired for a given application. The pores in the nozzles can have a variety of shapes and can be distributed in a variety of patterns. An elevated area can be formed around the exit aperture of the nozzle in order to prevent intrusion of liquid back into the nozzle. A method of producing an aerosolization device incorporating such a nozzle is also provided.

16 Claims, 1 Drawing Sheet

Figure 1A:
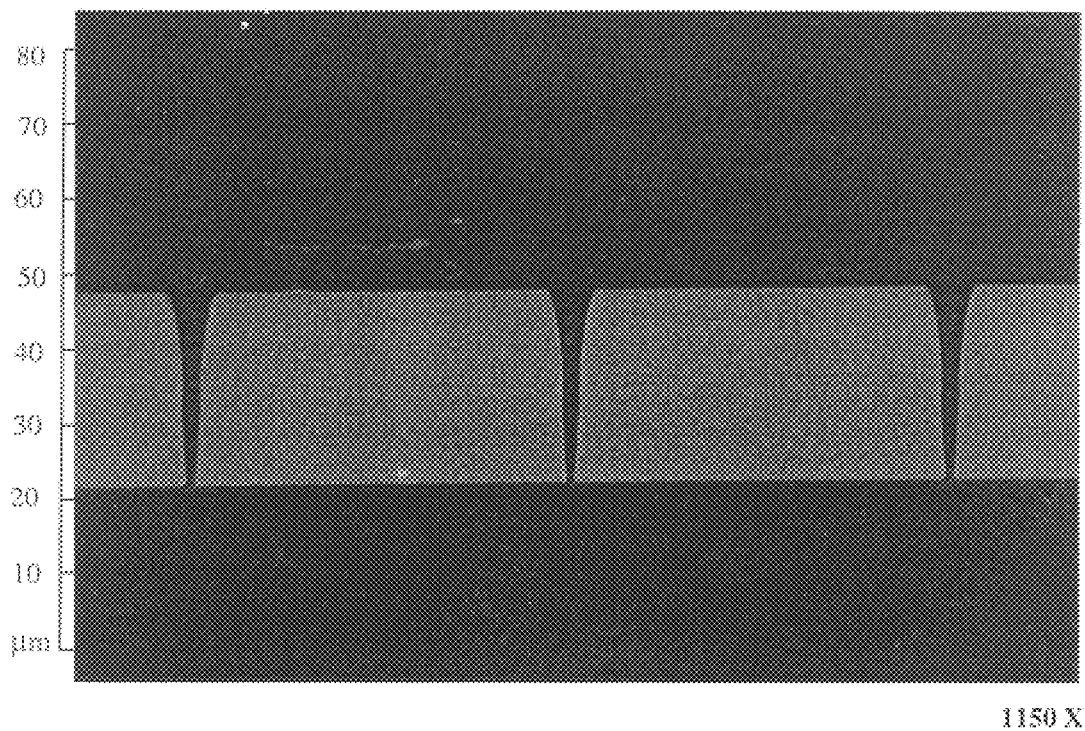

REACTIVE ION ETCHING METHOD OF FABRICATING NOZZLES FOR AEROSOLIZED DELIVERY OF THERAPEUTIC OR DIAGNOSTIC AGENTS

FIELD OF THE INVENTION

This invention relates generally to devices and methods for aerosolizing formulations. More specifically, this invention relates to methods of generating pores in an aerosolization nozzle comprising a membrane.

BACKGROUND OF THE INVENTION

In various areas of technology it is desirable to make use of a thin sheet of material which has an array of regularly spaced, very small holes therein. For example, such might be used in the manufacture of various electronic components. Thin membranes which have one or more holes in them could also be used in the formation of components used in ink jet printers or fuel injectors. A more direct application of such a porous membrane is as a filter. The pore size and pore density could be adjusted to wide range of filter applications. Alternatively, liquid formulations containing a drug could be moved through such a porous member to create an aerosol for inhalation.

Aerosolization is a desirable means for the delivery of therapeutic or diagnostic agents. Aerosol delivery avoids the problems associated with other delivery methods such as oral administration or injection. Injections are painful, present a risk of infection to the health-care provider from an inadvertent needle-stick, and create hazardous waste from the needle and syringe. Additionally, repeated injections can result in scarring. Oral administration must overcome several obstacles to the delivery of agents, including the acidic environment of the stomach, the ability of the agent to pass through the of the intestinal wall, and first-pass metabolism of the agent by the liver. Aerosol delivery, on the other hand, allows the direct delivery of agents to areas such as the nasal tract, the respiratory tract, or the eye, as well as systemic delivery into the circulation by administration to the respiratory tract and uptake into the circulation.

Currently available methods of generating and delivering aerosols to the nasal and respiratory tract include metered-dose inhalers, dry powder inhalers and nebulizers. Available methods of delivering agents to the eye include ointments and eye drops.

Co-owned U.S. Pat. Nos. 5,544,646; 5,718,222; 5,660,166; 5,823,178; 5,709,202; and 5,906,202 describe devices and methods useful in the generation of aerosols suitable for drug delivery. A drug formulation is forcibly applied to one side of a pore-containing membrane so as to produce an aerosol on the exit side of the membrane. Aerosols containing particles with a more uniform size distribution can be generated using such devices and methods, and can be delivered to particular locations within the respiratory tract.

Improved porous membranes for use in such devices would allow more efficient use of formulations, thereby requiring packaging of less formulation, decreasing costs and increasing portability, as well as increasing patient compliance. There is a need for methods of procuding nozzles for use in aerosolization of diagnostic or therapeutic agents.

SUMMARY OF THE INVENTION

The present invention provides an extrusion nozzle that is particularly well suited to extrusion of a formulation into the entraining airstream and delivery of particles having an improved size distribution to the respiratory tract. The nozzles of the invention maximize the conversion of pressure on the formulation container to kinetic energy of the formulation being extruded, and provide aerosol particles of the desired sizes.

The invention further provides a method of forming nozzles for aerosolization of diagnostic and therapeutic agents that allows unique control of the nozzle size and shape. The method generally comprises treating a membrane so as to form pores to a certain depth in the membrane, and further treating the membrane with a plasma, thereby further forming the pores.

The pores are preferably formed using a UV excimer laser having a wavelength of from about 150 nm to about 360 nm. The plasma is preferably an oxygen and argon plasma generated using radiofrequency energy source in a power range of from about 200 to about 800 watts.

In one embodiment, the nozzles are formed completely through the material prior to plasma treatment. In another embodiment, the nozzles are initially formed so that a thin layer remains covering the exit side of the nozzle. This layer can be removed during plasma treatment, or can be burst outwards upon administration of a formulation at a pressure substantially below that which would rupture the remainder of the membrane.

In one aspect of the invention, a method of producing a nozzle for aerosolizing a formulation is provided wherein from about 200 to about 1,000 holes are formed per square millimeter. In a particular embodiment, holes having an average relaxed exit aperture diameter of from about 0.5 to about 1.5 μm and spaced from about 30 to about 70 μm apart from each other are formed.

In one aspect of the invention, a neodymium-yttrium lithium fluoride laser is used as the laser source. In another aspect of the invention, the nozzles are formed so as to have an exit aperture of from about 0.5 to about 25 μm in diameter.

In another aspect of the invention, an oxygen and argon plasma is used to treat the laser-ablated material.

In another embodiment of the invention, a method for manufacturing a drug delivery device is provided wherein a nozzle array manufactured via laser ablation as described is functionally incorporated into an aerosol delivery device. The aerosol delivery device generally comprises a device for holding a container having at least one opening, wherein the opening leads to an open channel, a nozzle positioned at the end of the open channel, formulation in an amount of 100 milliliters or less in the container, and a mechanism for forcing the formulation through the nozzle.

One aspect of the invention is a nozzle for aerosolizing a formulation for respiratory delivery, said nozzle comprising a membrane having about 10 to about 1,000 pores per square millimeter, said pores having an average relaxed exit aperture diameter of from about 0.5 to about 5 μm and being spaced at a distance of from about 30 to about 70 μm apart from each other. The membrane is preferably flexible.

In a further aspect of the invention, a nozzle is provided wherein the area surrounding the exit aperture of the pores is elevated above the (otherwise substantially planar) exit side of the film so as to prevent intrusion of liquid into the exit aperture of the pores.

In another aspect of the invention, a nozzle is provided wherein the exit aperture of the pores has a smaller diameter than the entrance aperture.

In yet another aspect of the invention, a nozzle is provided wherein the pores are incompletely formed so that, upon administration of pressure to the entrance side of the film, the exit aperture is formed by bursting outward the exit side of the pores, thereby forming an elevated area preventing liquid intrusion into the exit aperture.

In a further aspect of the invention, a strip containing multiple nozzles is provided.

Another aspect of the invention is a method for aerosolizing a formulation in a way that maximizes the amount of formulation available for inhalation, comprising extruding the formulation into an airstream through a flexible, porous membrane, where the pores are from about 0.5 to about 1.5 micrometers in exit aperture diameter when unflexed, and are spaced about 30–70 $\mu$m apart.

Still another aspect of the invention is a method for aerosolizing a formulation through a nozzle comprising such pores where the area surrounding the exit aperture is elevated above the substantially planar exit side of the membrane.

Yet another aspect of the invention is a method for aerosolizing a formulation through pores having entrance apertures wider than their exit apertures.

These and other objects, advantages, and features of the invention will become apparent to those persons skilled in the art upon reading the details of the invention as more fully described below.

BRIEF DESCRIPTION OF THE DRAWINGS 1A and 1B show scanning electron micrograph images of pores formed using an exemplary embodiment of the methods of the invention.

MODES OF CARRYING OUT THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a pore" includes a plurality of such pores and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "porosity" is used herein to mean a percentage of an area of a surface area that is composed of open space, e.g., a nozzle, pore, hole, channel or other opening, in a membrane, filter or other material. The percent porosity is thus defined as the total area of open space divided by the area of the material, expressed as a percentage (multiplied by 100). High porosity (e.g., a porosity greater than 50%) is associated with high flow rates per unit area and low flow resistance. In general, the porosity of the nozzle is less than 10%, and can vary from $10^{-3}$% to $10^{-1}$%, while the porosity of the filter is at least 1%, and preferably it is at least 50% porous.

The term "porous membrane" shall be interpreted to mean a membrane of material having any given outer parameter shape, but preferably having a convex shape, wherein the membrane has one or more nozzles formed therein, which openings may be placed in a regular or irregular pattern, and which nozzles have an unflexed diameter of their exit aperture in the range of about 0.25 micron to about 6 microns and a nozzle density in the range of about 1 to about 1,000 nozzles per square millimeter for respiratory delivery. For ocular delivery, the nozzles have an unflexed diameter of their exit aperture in the range of about 5 microns to about 50 microns, preferably about 7.5 to about 25 microns, and a similar nozzle density. The porous membrane has a porosity of about 0.0005% to about 0.2%, preferably about 0.01% to about 0.1%. In one embodiment, the porous membrane comprises a single row of nozzles on, e.g., a large piece of membrane material. The nozzles may be planar with respect to the surface of the porous membrane material, or may have a conical configuration. The membrane material is preferably hydrophobic and includes materials such as polycarbonates and polyesters. The membrane preferably has sufficient structural integrity so that it is maintained intact (will not rupture) when subjected to force in the amount up to about 35 bar, preferably of up to about 50 bar while the formulation is forced through the nozzles.

The term "porous membrane" shall be interpreted to mean a membrane of material having any given outer parameter shape, but preferably having a convex shape, or being capable of flexing into a convex shape, wherein the membrane has a plurality of pores therein, which openings may be placed in a regular or irregular pattern. The pores of the membrane have an entrance diameter larger than the exit diameter, and the ratio of entrance:exit diameter is 5 or more to 1, preferably 10:1 or greater, more preferably 15:1 or greater, more preferably 25:1 or greater. Preferably, the membrane has pores which have an unflexed diameter of their exit aperture in the range of 0.25 micron to 6 microns and a pore density in the range of 1 to 1,000 pores per square millimeter for respiratory delivery. For ocular delivery, the pores have an unflexed diameter of their exit aperture in the range of 0.5 microns to 50 microns, generally 1.0 to 25 microns, and a similar pore density. The porous membrane has a porosity of about 0.0005% to 0.2%, preferably about 0.01% to 0.1%. In one embodiment, the porous membrane comprises a single row of pores on, e.g., a large piece of membrane material. The pores may be planar with respect to the surface of the porous membrane material, or may have a conical configuration.

For purposes of the present invention, a porous membrane has an entrance side, to which formulation is applied under pressure, and an exit side, from which the aerosol is released. The membrane also has a nozzle area, through which a plurality of pores passes. The pores pass substantially perpendicularly through the thickness of the membrane, from the entrance side to the exit side. Each pore has an entrance diameter (or cross-sectional area) and an exit diameter (or cross-sectional area).

A "tapered pore", as used herein, refers to a pore whose diameter and/or cross-sectional area decreases in a substantially continuous fashion from the entrance side to the exit side of the membrane.

A "stepped pore", or "multistep pore", as used herein, intends a pore whose diameter and/or cross-sectional area decreases in a stepwise, discontinuous fashion from the entrance side to the exit side of the porous membrane through which it passes, in contradistinction to the substantially continuous, linear decrease in diameter characteristic of a cone, or the uniform diameter of a cylinder. A "stepped pore" refers to a pore which has at least one abrupt change in pore size, but that abrupt change may be followed by a second smooth or continuous change in size, i.e., a pore step may be substantially cylindrical or cone-shaped. A "stepped pore" is a pore having a discontinuous cross-sectional profile, an example of which is shown schematically in FIG. 2. The term "pore step", as used herein, refers to a segment of a multistep pore. A pore step passes through a portion, having a height h, of the membrane material forming the nozzle, where h is less than the thickness of the membrane. The term "multistep pore" intends pores comprising two or more of such steps. Each step is progressively, and discontinuously, reduced in diameter relative to the preceding step, going from the entrance to exit side of the membrane, ultimately resulting in an exit aperture size capable of producing aerosol particles of the desired size. Said another way, the diameter of the pore decreases abruptly from one step to the next, going from the entrance side of the membrane to the exit side of the membrane. A given multistep pore is said to have a pore entrance aperture, i.e., the aperture on the entrance side of the membrane, and a pore exit aperture, i.e., the aperture on the exit side of the membrane. Similarly, a given pore step is said to have a pore step entrance aperture and a pore step exit aperture. Each aperture has a size. If a given aperture is roughly circular, then the size can be described as the diameter. If a given aperture is irregularly shaped, or otherwise non-circular, then the size can be described as the cross-sectional area at the aperture. The position of a given pore step relative to another pore step can be expressed in terms of proximity to the entrance or exit side of the membrane. Thus, for example, the entrance aperture size of a given pore step can be described in relation to the exit aperture size of the preceding "entrance proximal" pore step. The step of the pore immediately adjacent to the exit side of the membrane from which the aerosol is produced is referred to as the "through-step" or "exit-step."

Method of Fabricating Pores in Membranes

We have now invented a method of forming and modifying pores in a thin flexible organic polymer membrane that permit the generation of fine aerosols of diagnostic and therapeutic agents. The method comprises treating a thin, flexible material having partially formed pores with a plasma so as to etch the partially-formed pores, thereby modifying the pores. The etching process is typically carried out using a reactive ion etching method. Reactive ion etching of a partially formed pore alters one or more pore parameters, including pore shape, pore depth, and pore diameter. The material thus treated can be used directly, or can undergo further processing steps prior to incorporation into a device for delivering aerosols of diagnostic or therapeutic agents.

Initial Pore Formation

The pores in the membrane are initially partially formed through the membrane. By "partially formed" is meant that one or more pore parameters (including pore shape, pore depth, and pore diameter) will be further modified by plasma etching. A partially formed pore may or may not penetrate the thickness of the membrane. The pores in the membrane nozzles may be initially formed by any suitable method, including anisotropic etching, electroforming, electron discharge, or laser drilling. In some embodiments, pores are initially formed by laser drilling. The particular laser source used will to some extent be determined by the material in which the nozzles are to be formed. Generally, the laser source must supply a sufficient amount of energy of a wavelength which can form a nozzle effective for aerosolization from the material being used. One laser effective for creating nozzles in materials such as polyethers and polyimides is a neodymium-yttrium lithium fluoride. An example of a suitable laser source is an excimer laser.

The output of the particular source can be manipulated in a variety of ways prior to being applied to the material. For example, the frequency can doubled or tripled using, for example, a lithium triborate crystal or series of crystals using a type1 process, a type II process or a combination thereof.

Initial pore formation can be carried out using a variety of methods, including multi-step and single-step methods.

To form a multi-step pore, a first pore step is formed to a depth h1 (resulting in a first pore step height h1) in a membrane, starting from the entrance side of the membrane, wherein h1 is less than the thickness of the membrane, and is generally about 20% to about 90%, generally about 40% to about 80% of the thickness of the membrane. The first pore step has an entrance aperture size and an exit aperture size. A second pore step is then formed to a depth h2 (resulting in a second pore step height h2), which in turn has an entrance aperture size and an exit aperture size. The second pore step entrance aperture size is generally about 20% to about 90%, generally about 40% to about 80% of the first pore step aperture size. The second pore step exit aperture can also be the pore exit, or can lead to a third pore step. In general, the entrance aperture size of a given pore step is about 20% to about 90%, generally about 40% to about 80%, of the exit aperture size of the preceding, membrane entrance side-proximal, pore step.

For example, a two-step pore can be formed by directing about 40–60 pulses of an excimer laser beam at a fluence level of 625 mJ/cm$^2$ so as to form a 25 $\mu$m entrance aperture diameter first pore step to a depth of 10–20 $\mu$m through a 25 $\mu$m thick polyimide film, resulting in a first pore step having a height of 10–20 $\mu$m.

In some embodiments, laser ablation is used to form tapered or multi-step pores as described herein in the membrane. The particular laser source used in the method of the invention will to some extent be determined by the material in which the pores are to be formed. Generally, the laser source must supply a sufficient amount of energy of a wavelength which can form an effective aerosolization nozzle in the material being ablated. Typically, for an organic polymer membrane, the wavelength is from about 150 nm to about 360 nm.

The output of the particular laser source can be manipulated in a variety of ways prior to being applied to the material. For example, the frequency can doubled or tripled using, for example, a lithium triborate crystal or series of crystals, or a combination thereof. This laser beam can be further split into multiple beams to create multiple pores simultaneously. The beam can also be directed through a mask or spatially filtered, and can also be expanded prior to focusing.

One laser effective for such nozzles is a neodymium-yttrium aluminum garnet laser. This laser can be configured to provide a pulsed ultraviolet wavelength light source which provides sufficiently high peak power in short pulses to permit precise ablation in a thin material. The beam profile from this laser is radially symmetric which tends to produce radially symmetric pores.

Another laser effective for creating pores in materials such as polyethers and polyimides is an excimer laser. This laser also produces ultraviolet wavelength light. However, the beam is not radially symmetrical but is projected through a mask to simultaneously drill one or more conical or cylindrical holes. In some embodiments, the laser source is an excimer laser providing a wavelength of 308 nm. The energy density used for such a laser typically ranges from about 300 to about 800 mJ/cm$^2$, from about 400 mJ/cm$^2$ to about 700 mJ/cm$^2$, from about 500 mJ/cm$^2$ to about 700 mJ/cm$^2$. In some embodiments, the energy density is about 630 mJ/cm$^2$. Using such a laser on a 25 μm thick polyimide membrane, the number of pulses is typically about 40 to about 200. Those skilled in the art will readily appreciate that these parameters can be varied, depending on the thickness of the membrane being drilled.

The methods of the present invention for producing a porous membrane, generally comprise the steps of: directing laser energy onto an entrance surface of a membrane and continuing to direct the energy until the laser has created a pore having an entrance aperture and an exit aperture having a pore entrance aperture size and a pore exit aperture size, wherein the ratio of pore entrance aperture size to pore exit aperture size is at least about 10:1. The directing of laser energy can be repeated a plurality of times, by repositioning the laser energy for each directing step, or by repositioning the membrane for each directing step.

Any of a number of single-step methods are available for use in initial pore formation.

One such method makes use of a single mask having a variable-density dot pattern, as described in U.S. Pat. No. 5,417,897, which method is specific to making a hole for an ink jet printer nozzle. Using this method, a mask may comprise an open central region, which allows 100% transmission of the laser energy. Surrounding and continuous with the open central region is a second region in which the mask material is arranged in a pattern of opaque dots which act to partially shield a membrane in which pores are to be formed. By selecting a density of opaque dots in the peripheral region around the central opening, the central portion of each nozzle formed will be completely ablated through, and the peripheral portions of the nozzle will be only partially ablated. Transmission of laser energy in the first peripheral region is about 20 to about 65%. A second peripheral region can be made such that the transmission is less than in the first peripheral region. By varying the density of the opaque dots in the first and (optional) second peripheral regions, the pore formed in the nozzle membrane can be made to a desired shape. This process is sometimes referred to herein as a "Grayscale process".

Another method for making pores having the characteristics described above involves use of dithering, or rotating an optical mirror to rotate a laser beam during the ablation process. By changing the rotation of the mirror, the laser beam can be focused onto an area of successively decreasing size through the thickness of the membrane, thereby forming a reduced-pressure aerosolization pore having the characteristics described herein. The dithering method has been amply described in the literature, including, for example, in U.S. Pat. No. 4,894,115.

Plasma Etching

The pores thus formed or partially formed within the membrane are then treated with a plasma which modifies or completes the pores. The plasma comprises a partially ionized mixture that contains electrons, ions and neutral species at various levels of excitation. The plasma etches the material forming the pores, thereby altering their size and shape.

Plasma can be formed by any known process, using any known apparatus, including parallel plate-type apparatus and a high frequency induction-type apparatus, including, but not limited to, an apparatus such as that described in U.S. Pat. No. 5,938,883. The plasma can be generated and utilized by placing the membrane in a vacuum chamber, evacuating the chamber, filling the chamber with the gas which is to form the plasma, and subjecting the chamber to an energy source which ionizes the gas and thereby forms the plasma, whereupon the plasma reacts with the membrane. Alternatively, the plasma can be generated and utilized at atmospheric pressure, using any known method, including that described in U.S. Pat. No. 5,456,972. The energy source can be any suitable energy source which can ionize the gas to form the plasma, for example radiofrequency energy, and the like. Preferably, the energy source provides radiofrequency (RF) energy.

Typically, a mask is used which is not reactive with the plasma, or which is less reactive with the plasma than the membrane being treated, so that the pores are formed only where desired, i.e., at the locations of holes in the mask.

The parameters which can be varied include 1) choice of gas; 2) power level; 3) vacuum pressure; 4) etch time; and 5) gas flow.

The plasma can be any plasma which reacts with the material forming the nozzles and the membrane. Suitable gases used for generating a plasma can include oxygen, nitrogen, air, argon, helium, nitrous oxide, ammonia, $SF_6$, $C_2F_6$, $CHF_3$, $BCl_3$, water vapor, tetrafluoromethane ($CF_4$), and mixtures thereof. A preferred gas is a mixture of argon and oxygen.

In general, the gas/gas mixtures are subjected to from about 100 to about 800 Watts, from about 300 to about 500 watts, of RF energy.

Plasma is generally formed in a vacuum chamber. In general, the plasma is formed at pressures ranging from about 100 to about 500 mTorr.

Etch time can be varied, depending on the degree of etching desired, and in general ranges from about 60 to about 900 seconds, from about 300 to about 600 seconds. The etch rate typically ranges from about 10 to about 5000 Å/minute.

Gas flow typically ranges from about 10 to about 1000 $cm^3$/minute.

Plasma etching increases the hydrophilicity of the surface of the material forming the pores (i.e., the inner surface of the pore through which a liquid formulation passes). The process of plasma etching increases the hydrophilicity of the pore inner surface by at least about 10%, 20%, 30%, 40%, 50%, 75%, 100% (i.e., 2-fold), 2.5-fold, 5-fold, 10-fold or more. Whether the inner surface of the pore has increased hydrophilicity relative to a pore not subjected to plasma etching can be determined by measuring surface tension, using devices and techniques well known in the art, e.g., using a tensiometer.

Nozzle Materials

The membrane material is preferably hydrophobic and includes, but is not limited to, materials such as polycarbonates, polyimides, polyamides, polysulfone, polyolefin, polyurethane, polyethers, polyether imides, polyethylene and polyesters which may have the pores formed therein by any suitable method including, but not limited to, laser drilling, electron discharge machining, or anisotropic etching through a thin film of metal or other suitable material. Co-polymers of the foregoing can also be used. Shape memory polymers, which are known in the art and have been described in, inter alia, U.S. Pat. No. 5,910,357, can also be used. Preferably, the membrane is one that does not interact chemically with the substance being aerosolized, or the aerosolization solvent. The membrane preferably has sufficient structural integrity so that it is maintained intact (will not rupture) when subjected to force in the amount up to about 580 psi, preferably of up to about 725 psi, while the formulation is forced through the pores.

In some embodiments, the material is a flexible polymeric organic material, for example a polyether, polycarbonate, polyimide, polyether imide, polyethylene or polyester. Flexibility of the material is preferred so that the nozzle can adopt a convex shape and protrude into the airstream upon application of pressure, thus forming the aerosol away from the static boundary layer of air. Material which is substantially non-flexible can also be used, and, if such material is used, is preferably shaped to have a convex configuration.

As would be apparent to those skilled in the art who read this disclosure, the nozzle area is the porous membrane area. That area may be integral with surrounding sheet material (i.e. a porous area of sheet or tape) or be a separate membrane covering an opening in a thin sheet or tape (i.e., a porous membrane sheet separate from the surrounding sheet or tape). In some embodiments, the porous membrane is covered by a removable cover sheet detachably connected to the porous membrane.

The thickness of the membrane affects both the manufacturing of the nozzles and containers as well as the pressure required to generate the desired aerosol during administration. Thinner membranes require less pressure to generate an aerosol, but are conversely more difficult to handle during manufacturing, for example in laminating the membrane to other components of the formulation container. The membrane is preferably about 10 to about 100 μm in thickness, from about 15 to about 40 micrometers, from about 20 to about 30 micrometers, more preferably from about 12 to about 45 μm in thickness. In one embodiment, the membrane material is a 25 μm thick film of polyimide. Considerations for the membrane material include the ease of manufacture in combination with the formulation container, flexibility of the membrane, and the pressure required to generate an aerosol from pores spanning a membrane of a given material, thickness and flexibility.

Pore Characteristics

The cross-sectional profile of the pores can be discontinuous (i.e., multi-step), or continuous, (i.e., tapered). When the cross-sectional profile of a pore is discontinuous, the diameter and/or cross-sectional area of a given pore step is reduced in a step-wise fashion, relative to the preceding pore step. When the cross-sectional profile of a pore is tapered, the diameter from the entrance side to the exit side decreases in a substantially continuous fashion, i.e., there is a gradual diminution of diameter of the pore from the entrance side to the exit side. The pores may have an entrance aperture diameter to exit diameter ratio of at least about 10:1, more preferably at least about 12.5:1, more preferably at least about 15:1, more preferably at least about 20:1, more preferably at least about 25:1, up to about 100:1.

The pores can be of any shape, including, but not limited to, multi-step and tapered. Tapered pores are generally conical, where "conical" means that the pores are larger on one side of the membrane than on the other side, and that the diameter decreases in a continuous, linear fashion, i.e., a smooth curve, and includes instances where the cross-section of the pores is conical or curved. Multi-step pores can have two, three, four, or more steps, as necessary to achieve a reduction in the pressure needed to generate an aerosol. The number of steps is not critical to the aerosolization nozzles of the present invention. The height and aperture size of each pore step may depend upon the thickness of the membrane material. In some embodiments, the pore step adjacent to the entrance side of the membrane has a height of from about 20% to about 90%, usually from about 40% to about 80%, of the thickness of the material. Each pore step may be roughly cylindrical or conical in shape, where "cylindrical" means that the steps pass perpendicularly through the membrane and have approximately the same diameter throughout their length, and "conical" means that the pores are larger on one side of the membrane than on the other side, and that the diameter decreases in a continuous, linear fashion, and includes instances where the cross-section of the pores is conical or curved. In some embodiments, the through-steps are conical.

When the pores, pore steps, or through-steps of the pores are conical, the wider diameter of the cone is found on the entrance side of the pore to which the formulation is applied under pressure, while the smaller diameter of the cone is closer to the exit side of the pore from which aerosolization occurs. The exit aperture size of the pores is preferably uniform; following the methods taught herein, the variability in exit aperture size is generally less than about 10%, usually less than about 5%. The nozzle may be provided as an integral part of the formulation packaging, or may be provided separately, for example integrally with the inhalation device, or wound on a roll for disposable use.

The pore structures described herein are formed in a membrane for use in an aerosolization device, and allow generation of aerosols at significantly lower aerosolization pressures than was previously achievable. Accordingly, the pore structures of the present invention, when formed in membranes used in an aerosolization device, allow aerosolization of a flowable formulation at extrusion pressures less than about 500 psi, generally in a range of about 100 psi to about 500 psi, usually in a range of about 200 psi to about 400 psi. In general, the amount of pressure required is greater than about 100 psi, and less than about 500 psi.

For respiratory delivery, the pores are formed so as to have an unflexed exit aperture diameter from about 0.25 to 6.0 micrometers in size, from about 0.5 to 5.0 μm, and in some embodiments, from about 0.5 to about 2 μm. When the pores have this size, the droplets that are formed will have a diameter about twice the diameter of the pore size. In some cases, it may be desirable to generate aerosols having an aerodynamic size in a particular range. Thus, it may be of interest to generate particles having an aerodynamic size in the range of 1–3 μm, 4–6 μm, or 7–10 μm. Exit pore aperture sizes would be adjusted accordingly.

Generally, the pores are spaced about 30 to about 70 μm apart, preferably about 50 μm apart. The spacing is preferably fairly uniform. For ocular delivery, the nozzles are formed so as to have an unflexed exit aperture diameter in the range of about 5 microns to about 50 microns, preferably 7.5 to 25 microns.

The terms "particle diameter", "particle size" and the like are used interchangeably herein to refer to particle size as given in the "aerodynamic" size of the particle. The aerodynamic diameter is a measurement of a particle of unit density that has the same terminal sedimentation velocity in air under normal atmospheric conditions as the particle in question. When small (e.g., 1–50 micrometer diameter) particles are said to have the same diameter, they have the same terminal sedimentation velocity. This is pointed out in that it is difficult to accurately measure the diameter of small particles using current technology and the shape of such small particles may be continually changing. For ocular delivery, the pores are formed so as to have an unflexed exit aperture diameter in the range of 5 microns to 50 microns, preferably 7.5 to 25 microns.

The pores can be spaced from about 10 to about 1000 μm apart or more, but are preferably spaced from about 30 to about 70 μm apart, most preferably about 50 μm apart. The pore spacing is determined in part by the need to prevent the aerosol from adjacent pores from adversely interfering with each other, and in part to minimize the amount of membrane used and the associated manufacturing difficulties and costs. The pore spacing is preferably fairly uniform, with a variability in the interpore distance of preferably less than about 20%, more preferably less than about 10%, and most preferably about 2% or less (<1 μm variability for pores spaced 50 μm apart).

The pores in a nozzle area may be arranged in regular arrays, such as in rows or grids of pores at regular, substantially uniform distances from one another. In one embodiment of the invention, the pores are formed in a 7×48 array of pores spaced 50 μm apart.

A given membrane may have a plurality of nozzle areas, at a given distance from an adjacent nozzle area, and separated from adjacent nozzle area by a section of non-porous membrane. In some embodiments, the membrane is a strip comprising a plurality of nozzle areas separated from one another by non-porous membrane areas.

The amount of liquid being aerosolized is generally from about 10 μl to about 100 milliliters. In some embodiments, the amount of liquid is in a range of from about 5 milliliters (ml) to about 100 milliliters, from about 10 milliliters to about 90 milliliters, from about 20 milliliters to about 80 milliliters, from about 40 milliliters to about 60 milliliters. In other embodiments, the amount of liquid is in a range of from about 0.5 ml to about 10 ml, from about 1 ml to about 8 ml, from about 2 ml to about 6 ml. In still other embodiments, the amount of liquid is in a range of from about 10 μl to about 1000 μl, from about 20 μl to about 100 μl.

The density of pores in the nozzle area ranges from 1 to about 1,000 pores, generally about 100 to about 900 pores, per square millimeter. In some embodiments, the pore density in the nozzle area is about 100 pores per square millimeter. In other embodiments, this density is about 200 pores per square millimeter.

The period of time over which the formulation is to be administered must also be considered. The delivery time is a critical parameter, as it is necessary to generate the aerosol during a sufficiently short period of time so that the aerosol may be targeted to a specific area of the respiratory tract during inspiration. For a given pore exit diameter and formulation pressure, hole number can be adjusted to control delivery time. Generally, aerosolization will occur within about 0.5 to about 5 seconds, usually in a range of about 1 second to about 2 seconds.

In one embodiment, the pores are incompletely formed so that a thin peelable layer remains covering the exit apertures of the pores. This peelable layer bursts outward upon forcible application of the drug formulation to the nozzle during drug delivery, permitting aerosolization of the formulation. The peelable layer of the pores is formed so as to have a breaking pressure significantly below that of the overall membrane, and the pressure at which the layer bursts is significantly below that applied in the normal course of drug administration, so that the pores burst substantially uniformly and completely. The incompletely formed pores may be formed by application of a thin layer of material to the outer side of the membrane after formation of complete pores, or by incompletely ablating holes through the membrane.

In another embodiment, the pores are provided with elevated areas surrounding the exit aperture, so as to prevent liquid from intruding from the outer surface of the membrane back into the pore and thereby disrupting aerosolization. The elevated areas may be of any shape, such as circular or rectangular, or may be irregularly shaped. The elevated areas can be constructed by any suitable means, for example by etching away portions of the outer layer of the membrane, by laser drilling procedures which lead to sputtering of material around the pores, by molding or casting, by deposition of material via a mask in locations where pores are to be formed, and the like.

A pore may be formed so as to have an elevated area via excimer laser ablation from the opposite side of the membrane. The formation of the elevated area via excimer laser ablation can be controlled by altering the pulse number: a minimal number of pulses used to penetrate the membrane will form an elevated area around the aperture on the opposite side of the membrane; increasing the number of pulses will then remove this elevated area. For example, for a 25 micron thick polyimide membrane, 120 pulses of a 308 nm excimer laser at an energy density of 630 mJ/cm$^2$ will form a pore having an elevated area, while increasing the number of pulses above 150 will remove the elevated area and slightly widen the pore aperture. The elevated areas may be of any suitable dimensions, but preferably extend significantly less than the interpore distance so as to provide lower areas where fluid is sequestered. The elevated areas can be made from any suitable material, for example the material comprising the bulk of the membrane, or may be made from materials with desirable properties such as hydrophobicity or solvent or drug repellence so as to repel the drug formulation from entering the exit aperture of the pores.

Nozzle Characteristics

The nozzles may be roughly cylindrical or conical in shape, where "cylindrical" means that the nozzles pass perpendicularly through the membrane and have approximately the same diameter on each surface of and throughout the membrane, and "conical" means that the nozzles are larger on one side of the membrane than on the other side, and includes instances where the cross-section of the nozzles is conical, curved or where the diameter of the nozzle is reduced stepwise. When the nozzles are conical, the wider diameter of the cone is found on the entrance side of the nozzle to which the formulation is applied under pressure, while the smaller diameter of the cone is found on the exit side of the nozzle from which aerosolization occurs. The nozzles may also be formed at diverging angles within the membrane so that the particle streams are directed in different, nonparallel directions so as to reduce particle-particle interactions. The nozzle may be provided as an integral part of the formulation packaging, or may be provided separately, for example integrally with the inhalation device, or wound on a roll for disposable use.

In an alternative embodiment, the nozzles are formed so that a thin burstable layer remains covering the exit apertures of the nozzles. This burstable layer bursts outward upon forcible application of the drug formulation to the nozzle during drug delivery, permitting aerosolization of the formulation. The burstable layer of the nozzles is formed so as to have a breaking pressure significantly below that of the overall membrane and significantly below the pressure applied in the normal course of drug administration, so that the nozzles burst substantially uniformly and completely. The burstable nozzles can be formed by forming nozzles which do not span the membrane, or can be formed by application of a thin layer of material to the outer side of the membrane after formation of nozzles that do span the membrane.

In a preferred embodiment, the nozzles are provided with elevated areas surrounding the exit aperture, so as to prevent liquid from intruding from the outer surface of the membrane into the nozzle and thereby disrupt aerosolization. The elevated areas may be of any shape, such as circular or rectangular, or may be irregularly shaped. The elevated areas can be constructed by any suitable means, for example by etching away portions of the outer layer of the membrane, by laser drilling procedures which lead to sputtering of material around the nozzles, by molding or casting, by deposition of material via a mask in locations where nozzles are to be formed, and the like. The elevated areas may be of any suitable dimensions, but preferably extend significantly less than the internozzle distance so as to provide lowered areas where fluid is sequestered. The elevated areas can be made from any suitable material, for example the material comprising the bulk of the membrane, or may be made from materials with desirable properties such as hydrophobicity or solvent or drug repellence so as to repel the drug formulation from entering the exit aperture of the nozzles.

Aerosolizatrion Devices

The present invention further provides aerosol delivery devices which comprise an aerosolization nozzle as described herein. In general, aerosol delivery devices useful with the invention comprise (a) a device for holding a formulation-containing container, preferably a disposable container, with at least one but preferably a number of containers, and (b) a mechanical mechanism for forcing the contents of a container (on the package) through a nozzle comprised of a porous membrane as provided by the present invention, optionally preceded by a low resistance filter. Where the device is used for respiratory delivery, the device can further comprise (c) a means for controlling the inspiratory flow profile, (d) a means for controlling the volume in which the drug or diagnostic agent is inhaled, (e) a switch for automatically releasing or firing the mechanical means to release a determined volume of aerosol and aerosol-free air when the inspiratory flow rate and/or volume reaches a predetermined point, (f) a means for holding and moving one package after another into a drug release position so that a new package is positioned in place for each release of drug, and (g) a source of power, e.g., spring, or conventional batteries or other source of electric power.

Examples of preferred inhalation devices for use in conjunction with the aerosolization nozzles of the present invention are those described in U.S. Pat. Nos. 5,622,162; 5,608,647; 5,934,272; 5,915,378; 5,906,202, incorporated herein by reference.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celcius, and pressure is at or near atmospheric.

Example 1

Preparation of Nozzles

Nozzles were prepared from thin-film polyimide (25 $\mu$m, Kapton™ Type 100H, DuPont) using a laser (Uniphase, model s349B-100Q). The film was held by a vacuum platen to a three axis stage.

To determine the effect of power level and number of pulses on pore size, the power and pulse number was varied in a systematic fashion as pores were drilled in a single piece of Katon™. A second order polynomial fit of the pore size vs. power level was performed, and was used to estimate the power required to drill pores of diameter 1, 1.5, and 2 $\mu$m. Sample nozzles were fabricated at various power levels, and pores on each sample were sized, and the average size computed. This process was iterated until a power level was determined that gave an average pore size within 5% of the desired value.

TABLE I

Power Level vs Pore Size

| Desired Pore Size | Power Level Used |
| --- | --- |
| 1.0 $\mu$m | 1.12 mW |
| 1.5 $\mu$m | 1.54 mW |
| 2.0 $\mu$m | 1.92 mW |

Nozzles for the experiments below were fabricated at these settings. The power was checked and adjusted after every 10 nozzles.

After laser ablation, pores were treated with oxygen and argon plasma to modify the cross-sectional profile (e.g., depth through membrane; cross-sectional area of entrance aperture and exit aperture) of the pores.

The etching of the partially-formed pores was controlled by adjusting RF power, gas flow rate, and time (i.e., duration) of etching. The parameters varied are shown in Table 2, below.

TABLE 2

| Sample | Ar/O₂ flow rate | RF power, Watts | Partially-formed pore diameter, $\mu$m | Modified pore diameter, $\mu$m | Duration, seconds |
|---|---|---|---|---|---|
| 1 | 500 | 300 | 1.17 | 1.74 | 300 |
| 2 | 500 | 400 | 1.17 |  | 300 |
| 3 | 1000 | 500 | 1.17 | 1.84 | 300 |
| 4 | 500 | 300 | 1.17 | 1.74 | 600 |
| 5 | 1000 | 400 | 1.17 | 2.97 | 600 |
| 6 | 1000 | 500 | 1.17 | 3.89 | 600 |

As shown in Table 2, there is a significant change in the cross-sectional profile of the pores as the power and duration are increased. These modifications were found to be reproducible.

To determine pore size, nozzles were imaged using a scanning electron microscope (Philips, model 505). The samples were coated by gold deposition (Denton Desk II, 45 $\mu$A, 120 seconds) prior to imaging. The images were digitized at video resolution using a frame grabber (Data translation DT3152). Video frames (64) were averaged to create a final image, which was store to disk. After 10 images had been acquired in this manner, they were read into an image processing software package (Optimus, version 6.0). A macro was developed that determined the preimeter of the pores by thresholding, and based on this perimeter, an area equivalent diameter was calculated. The area equivalent diameter determined for the 10 pores was averaged to determine the final diameter.

Figure 1B:
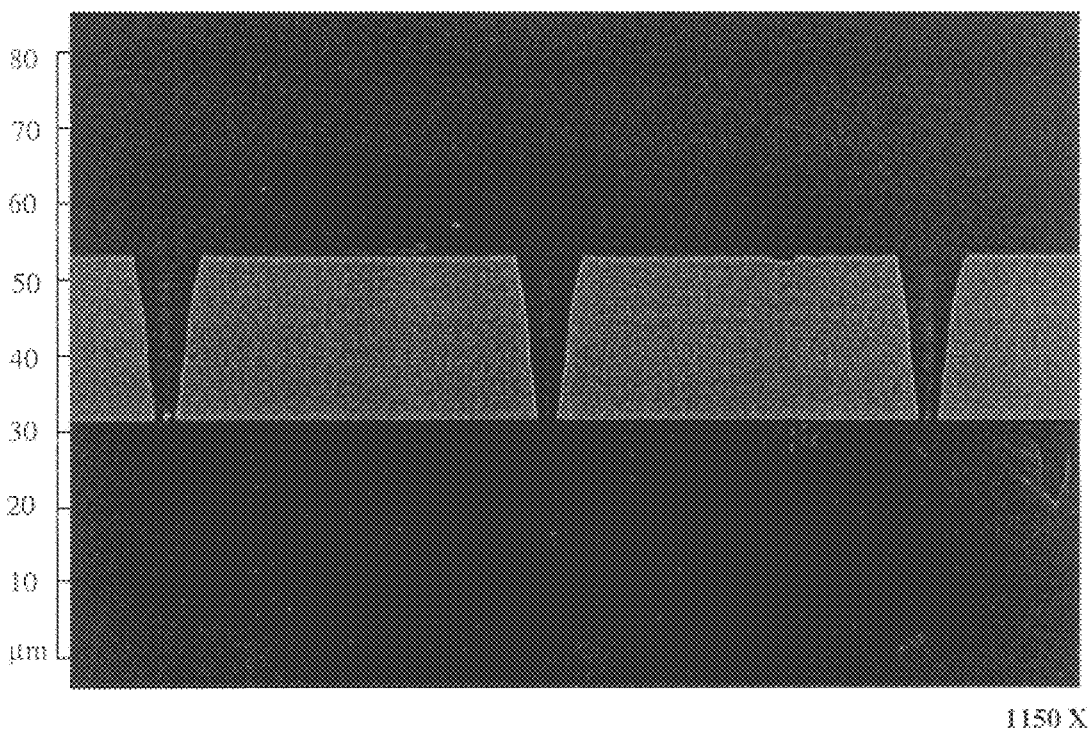

Examples of pores formed by laser ablation are shown in FIG. 1A. These pores were subjected to plasma etching at 500 watts of RF power for 600 seconds at argon and oxygen flow rates of 500 cm³/minute, resulting in the plasma-etched pores shown in FIG. 1B.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of producing a porous membrane, comprising the steps of:

directing laser energy onto an entrance surface of a flexible membrane and continuing to direct the energy until the laser has created a plurality of pores in the membrane, thereby forming a membrane comprising a plurality of partially formed pores;

exposing the membrane comprising partially formed pores to a reactive plasma, thereby creating plasma-etched pores, wherein the plasma-etched pores are positioned at a distance of about 30 to about 70 micrometers apart, and modified pore density is at least about 100 pores per square millimeter.

2. The method of claim 1, wherein the laser source is a UV excimer laser having a wavelength of from about 150 nm to about 360 nm.

3. The method of claim 2, wherein the excimer energy density is from about 300 to about 800 mJ/cm².

4. The method of claim 1, wherein the plasma is an oxygen and argon plasma.

5. The method of claim 4, wherein plasma is generated using radiofrequency in a power range of from about 200 to about 800 watts.

6. The method of claim 4, wherein the flow rate of argon and oxygen during the plasma treatment is from about 200 to about 1000 cubic centimeters per minute.

7. The method of claim 1, wherein the membrane is a polymeric organic membrane.

8. The method of claim 7, wherein the membrane is selected from the group consisting of polycarbonates, polyimides, polyethers, polyether imides, polyethylene and polyesters.

9. The method of claim 1, wherein the membrane is a polymeric organic membrane having a thickness in a range of about 10 to about 100 $\mu$m.

10. The method of claim 9, wherein the thickness is in the range of about 20 to 30 microns.

11. The method of claim 1, wherein the plasma-etched pore is formed completely through said membrane.

12. The method of claim 1, wherein the plasma-etched pore is not completely formed, but has a burstable layer of material at an exit end of the pore, and wherein the layer bursts upon application of a pressure that does not otherwise rupture the membrane.

13. The method of claim 1, wherein the nozzle is formed so as to have an elevated area projecting above the membrane surrounding an exit aperture of the nozzle.

14. The method of claim 1, wherein each of said plasma-etched pores has an exit aperture having a diameter in a range of from about 0.5 to about 25 $\mu$m.

15. The method of claim 14, wherein each of said plasma-etched pores has an entrance aperture size and an exit aperture size, wherein the entrance aperture size to exit aperture size ratio is at least about 10:1.

16. The method of claim 1, wherein the pores are formed regularly spaced in the membrane in rows.

* * * * *